(12) United States Patent
Tajima et al.

(10) Patent No.: US 10,869,998 B2
(45) Date of Patent: Dec. 22, 2020

(54) APPLICATOR

(71) Applicant: HISAMITSU PHARMACEUTICAL CO., INC., Tosu (JP)

(72) Inventors: Takuya Tajima, Tsukuba (JP); Naoki Yamamoto, Tsukuba (JP); Kazuki Kuriyama, Tsukuba (JP); Seiji Tokumoto, Tsukuba (JP)

(73) Assignee: HISAMITSU PHARMACEUTICAL CO., INC., Tosu (JP)

(*) Notice: Subject to any disclaimer, the term of this patent is extended or adjusted under 35 U.S.C. 154(b) by 86 days.

(21) Appl. No.: 16/078,784

(22) PCT Filed: Feb. 15, 2017

(86) PCT No.: PCT/JP2017/005510
§ 371 (c)(1),
(2) Date: Aug. 22, 2018

(87) PCT Pub. No.: WO2017/145891
PCT Pub. Date: Aug. 31, 2017

(65) Prior Publication Data
US 2019/0046779 A1 Feb. 14, 2019

(30) Foreign Application Priority Data

Feb. 24, 2016 (JP) ................. 2016-033441

(51) Int. Cl.
*A61M 37/00* (2006.01)
*A61F 13/00* (2006.01)

(52) U.S. Cl.
CPC ... *A61M 37/0015* (2013.01); *A61F 13/00085* (2013.01); *A61M 2037/0023* (2013.01)

(58) Field of Classification Search
CPC .......... A61M 37/0015; A61F 13/00085; A61F 15/005
See application file for complete search history.

(56) References Cited

U.S. PATENT DOCUMENTS

| | | |
|---|---|---|
| 2015/0290444 A1 | 10/2015 | Wirtanen et al. |
| 2016/0144160 A1 | 5/2016 | Yamamoto et al. |
| 2017/0333690 A1 | 11/2017 | Ogura et al. |

FOREIGN PATENT DOCUMENTS

| | | |
|---|---|---|
| CN | 103764197 A | 4/2014 |
| CN | 104736192 A | 6/2015 |

(Continued)

OTHER PUBLICATIONS

Extended European Search Report dated Aug. 17, 2020 corresponding to application No. 17885207.5.

(Continued)

*Primary Examiner* — William R Carpenter
(74) *Attorney, Agent, or Firm* — Nath, Goldberg & Meyer; Joshua B. Goldberg; Tanya E. Harkins

(57) ABSTRACT

An applicator according to one embodiment is an applicator for applying a sheet member to skin, and includes: a bottom plate facing the skin; a top plate facing the bottom plate and configured to be pressed toward the bottom plate; and a bending portion configured to apply the sheet member to the skin by bending the sheet member having advanced to the bending portion in a pressed state in which the top plate has been moved toward the bottom plate.

6 Claims, 17 Drawing Sheets

(56) References Cited

FOREIGN PATENT DOCUMENTS

| CN | 105324148 A | 2/2016 | | |
|---|---|---|---|---|
| EP | 1299147 A0 | 4/2003 | | |
| JP | 2005-118428 A | 5/2005 | | |
| JP | 2014200979 A | 10/2014 | | |
| TW | 201325643 A | 7/2013 | | |
| TW | 201519923 A | 6/2015 | | |
| WO | 02/02177 A1 | 1/2002 | | |
| WO | 0202180 A2 | 1/2002 | | |
| WO | WO-2014058746 A1 * | 4/2014 | ........ | A61M 37/0015 |
| WO | 2014/203910 A1 | 12/2014 | | |
| WO | 2015129545 A1 | 9/2015 | | |
| WO | 2016088886 A1 | 6/2016 | | |

OTHER PUBLICATIONS

Japanese Office Action dated Sep. 1, 2020 corresponding to application No. 2019-209852.

* cited by examiner

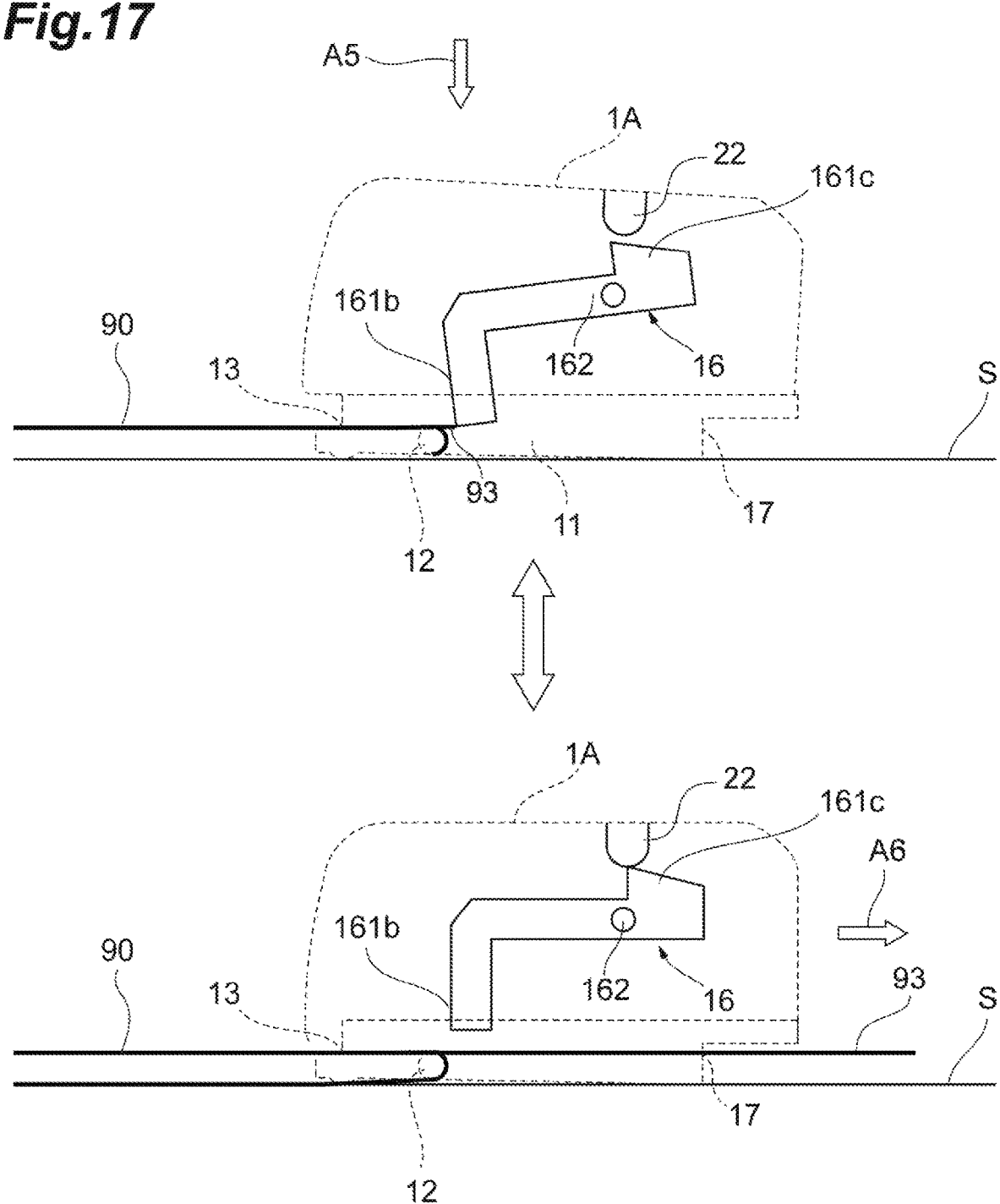

APPLICATOR

This is a National Phase Application filed under 35 U.S.C. 371 as a national stage of PCT/JP2017/005510, filed Feb. 15, 2017, an application claiming the benefit of Japanese Application No. 2016-033441, filed Feb. 24, 2016, the content of each of which is hereby incorporated by reference in its entirety.

TECHNICAL FIELD

One aspect of the present invention relates to an applicator used for assisting administration of an active ingredient.

BACKGROUND ART

A sheet member for enabling transdermal administration of an active ingredient has conventionally been known. Examples of such a sheet member include a patch disclosed in Patent Document 1 below, and a microneedle sheet illustrated in FIG. 1. An instrument for assisting the placement of a sheet member is also known, and Patent Document 1 discloses an assisting instrument for a patch. The assisting instrument includes a support body that has a surface with an area larger than that of a patch, an adhesive face that is one surface of the support body applied with a pressure-sensitive adhesive and that temporarily holds the patch in a removable manner, and a non-adhesive face.

CITATION LIST

Patent Literature

Patent Document 1: WO 2002/002177

SUMMARY OF INVENTION

Technical Problem

As an example, when the assisting instrument disclosed in Patent Document 1 is used, it is sometimes difficult to remove a release sheet from the patch once the patch is placed on the adhesive face of the support body, because the adhesive face is substantially flat. A possible solution for addressing this issue is to remove the release sheet from the patch before placing the patch on the adhesive face of the assisting instrument. However, once the release sheet is removed, the adhesive layer of the patch may stick together or become wrinkled, due to the flexibility of the patch.

In the microneedle sheet mentioned as another example (see FIG. 1), because a plurality of microneedles are provided in a manner laid along the principle surface of the sheet, it is necessary to raise the microneedles from the principle surface to insert the microneedles into the skin.

In this manner, depending on the type of sheet members, there are various types of demands. Therefore, it will be convenient if there is an applicator enabling any sheet member to be applied appropriately to the skin, regardless of the type of the sheet member.

Solution to Problem

An applicator according to one aspect of the present invention is an applicator for applying a sheet member to skin, the applicator including: a bottom plate facing the skin; a top plate facing the bottom plate and configured to be pressed down toward the bottom plate; and a bending portion configured to apply the sheet member to the skin by bending the sheet member having advanced thereto in a pressed state in which the top plate has been moved toward the bottom plate.

According to this aspect, the bending portion is configured to apply the sheet member to the skin by bending the sheet member having advanced thereto in a configuration in which the applicator (more specifically, the top plate) has been moved toward the skin. With this mechanism, pressing force at a certain level or higher is applied to the sheet member when the sheet member is applied to the skin. Therefore, whoever the person using the applicator is, the sheet member can be appropriately applied to the skin.

Advantageous Effects of Invention

According to one aspect of the present invention, a sheet member can be applied appropriately to the skin.

BRIEF DESCRIPTION OF DRAWINGS

FIG. 17 shows how the applicator according to the third embodiment is used.

DESCRIPTION OF EMBODIMENTS

Figure 1:
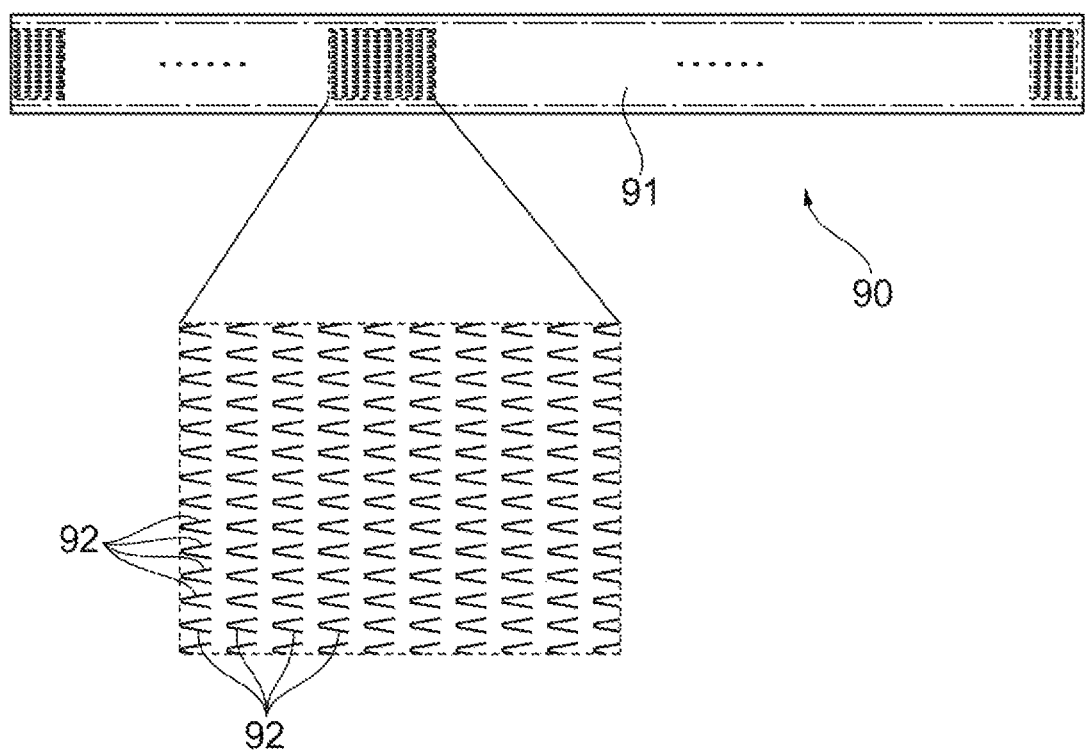
FIG. 1 is a plan view of a microneedle sheet used with an applicator according to a first embodiment and a second embodiment.

Some embodiments of the present invention will now be explained in detail with reference to the appended drawings. In the explanations of the drawings, the same reference numerals are assigned to the same or equivalent elements, and redundant explanations thereof will be omitted.

First Embodiment

An applicator is an assisting instrument used in applying, to skin, a sheet member for administering an active ingredient (such as a medication) into a living body. The sheet member to be applied to the skin using the applicator is not limited to a particular one, and examples of the sheet member include a patch and a microneedle sheet. By using the applicator, a user can apply a sheet member to the skin at a more appropriate force, compared with when the sheet member is applied directly to the skin by hand.

In this embodiment, a microneedle sheet is presented as an example of the sheet member. A microneedle sheet 90 that is used with the applicator 1 according to the first embodiment will now be explained with reference to FIG. 1. FIG. 1 is a plan view of the microneedle sheet. As illustrated in this figure, the microneedle sheet 90 has a band-like shape and has a plurality of microneedles 92 provided on the sheet, in a manner substantially laid along the principle surface 91 of the sheet. These microneedles 92 are arranged in a manner aligned in the longitudinal and the width directions of the sheet, and the tip of every microneedle 92 is directed toward one end of the sheet (the left side in FIG. 1) without any exception. The direction to which the tips of the microneedles 92 point matches the direction in which the microneedle sheet 90 advances during the use of the microneedle sheet 90.

The materials of the microneedle sheet 90 and the microneedles 92 are not limited to any particular materials. For example, the microneedle sheet 90 and the microneedles 92 may be fabricated using any of stainless steel, polyethylene terephthalate (PET), another type of metal, another type of resin, a biodegradable material, a ceramic, or a bioabsorbable material. Alternatively, the microneedle sheet 90 and the microneedles 92 may be fabricated using combinations of any of these materials.

The microneedles 92 may be formed by etching. When the sheet is made of a metal, the microneedles 92 may be formed by removing parts of the sheet with a chemical. When the sheet is made of a non-metallic material, the microneedles 92 may be formed by cutting some parts of the sheet using a laser. In these cases, some gaps are formed around the microneedles 92. It is, of course, possible to form the microneedles 92 using any other technique other than laser machining or etching. In this embodiment, the microneedles 92 have a triangular shape, as illustrated in FIG. 1, but the shape of the microneedles is not limited to any particular shape. In any case, because it is not necessary to raise the microneedles 92 from the principle surface 91 of the sheet in advance, the microneedle sheet 90 can be manufactured easily and inexpensively.

The size of the microneedle sheet 90 is also not limited to any particular size. Specifically, the lower limit of the thickness may be 5 micrometers or 20 micrometers, and the upper limit of the thickness may be 1000 micrometers or 300 micrometers. The lower limit of the length may be 0.1 centimeter or 1 centimeter, and the upper limit of the length may be 50 centimeters or 20 centimeters. The lower limit of the width may be 0.1 centimeter or 1 centimeter, and the upper limit of the width may be 60 centimeters or 30 centimeters. The lower limits of the length and the width of the microneedle sheet 90 are decided considering the dosage of the active ingredient, and the upper limits of the length and the width are decided considering the size of the living body.

Parameters related to the microneedles 92 are also not limited to any particular values. Specifically, the lower limit of the height of the needles may be 10 micrometers or 100 micrometers, and the upper limit of the height may be 10000 micrometers or 1000 micrometers. The lower limit of the density of the needles may be 0.05 per centimeters square or 1 per centimeters square, and the upper limit of the density may be 10000 per centimeters square or 5000 per centimeters square. The lower limit of the density is a value calculated from the number of needles and the area by which 1 milligram of active ingredient can be administered, and the upper limit of the density is the limit considering the shape of the needle.

Available as a method for preparing for the administration of the active ingredient to be applied to the skin are a method of coating the active ingredient on the microneedle sheet 90 itself; a method of applying the active ingredient to the skin before the microneedles 92 are inserted into the skin; and a method of applying the active ingredient to the skin after the microneedles 92 are inserted into the skin. When the active ingredient is coated on the microneedle sheet 90 in advance, it is preferable for a coat predetermined viscosity to be applied to the entire sheet, at a thickness as even as possible. The coat can be easily applied in such a manner, because the microneedles 92 are formed in a manner laid along the principle surface 91. The coat may be applied using a principle of screen printing, or in any other ways. When a biodegradable sheet is used, the sheet itself may contain the active ingredient, in advance.

The microneedle sheet 90 may be provided in a manner protected with a liner. An example of the material of the liner includes plastic such as acrylic resin, but the material is not limited to any particular one, and the liner may also be fabricated using a metal or another type of resin, for example. The microneedle sheet 90 is fixed to or temporarily bonded to one side of the liner using a tape or an adhesive.

Because the microneedles 92 are substantially laid along the principle surface 91 of the sheet until the microneedle sheet 90 is bent by the applicator, there is no concerns about the microneedles 92 scratching or getting caught by another object (such as skin or clothing of a user) unless the applicator is used. Therefore, the safety in handling the microneedles 92 can be ensured. For example, a user can store or carry the microneedle sheet 90 safely, or make preparations immediately before the use of the microneedle sheet 90 safely.

Figure 2:
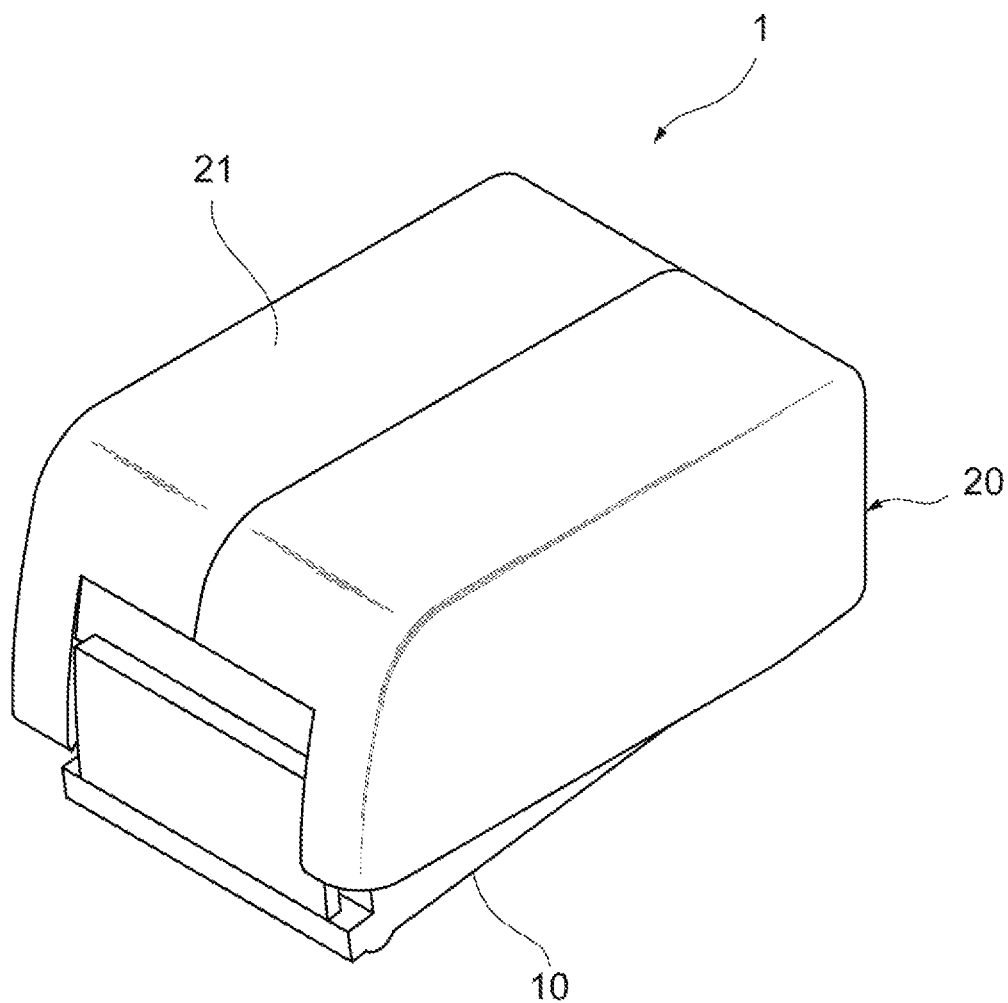
FIG. 2 is a perspective view from above, illustrating the applicator according to the first embodiment.
Figure 3:
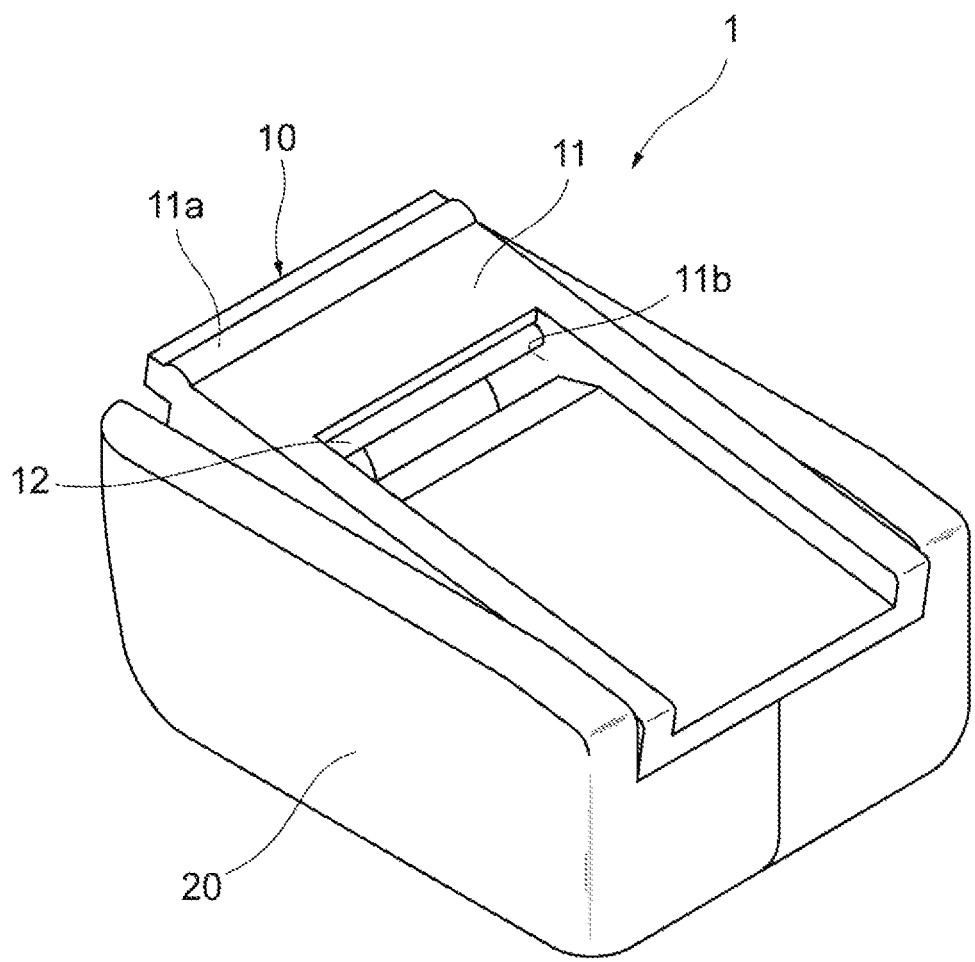
FIG. 3 is a perspective view from below, illustrating the applicator according to the first embodiment.
Figure 4:
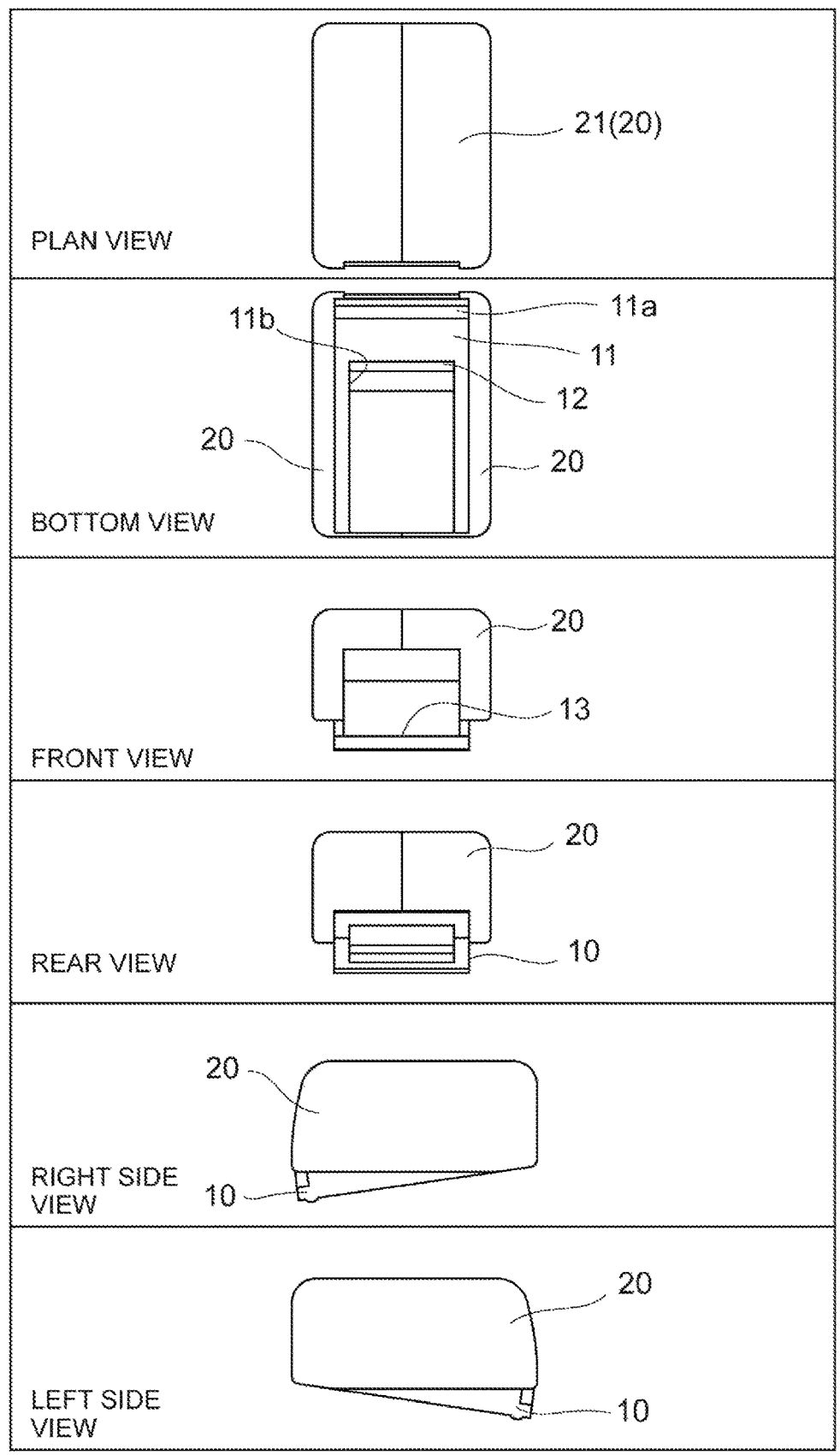
FIG. 4 is a schematic illustrating six sides of the applicator according to the first embodiment.
Figure 5:
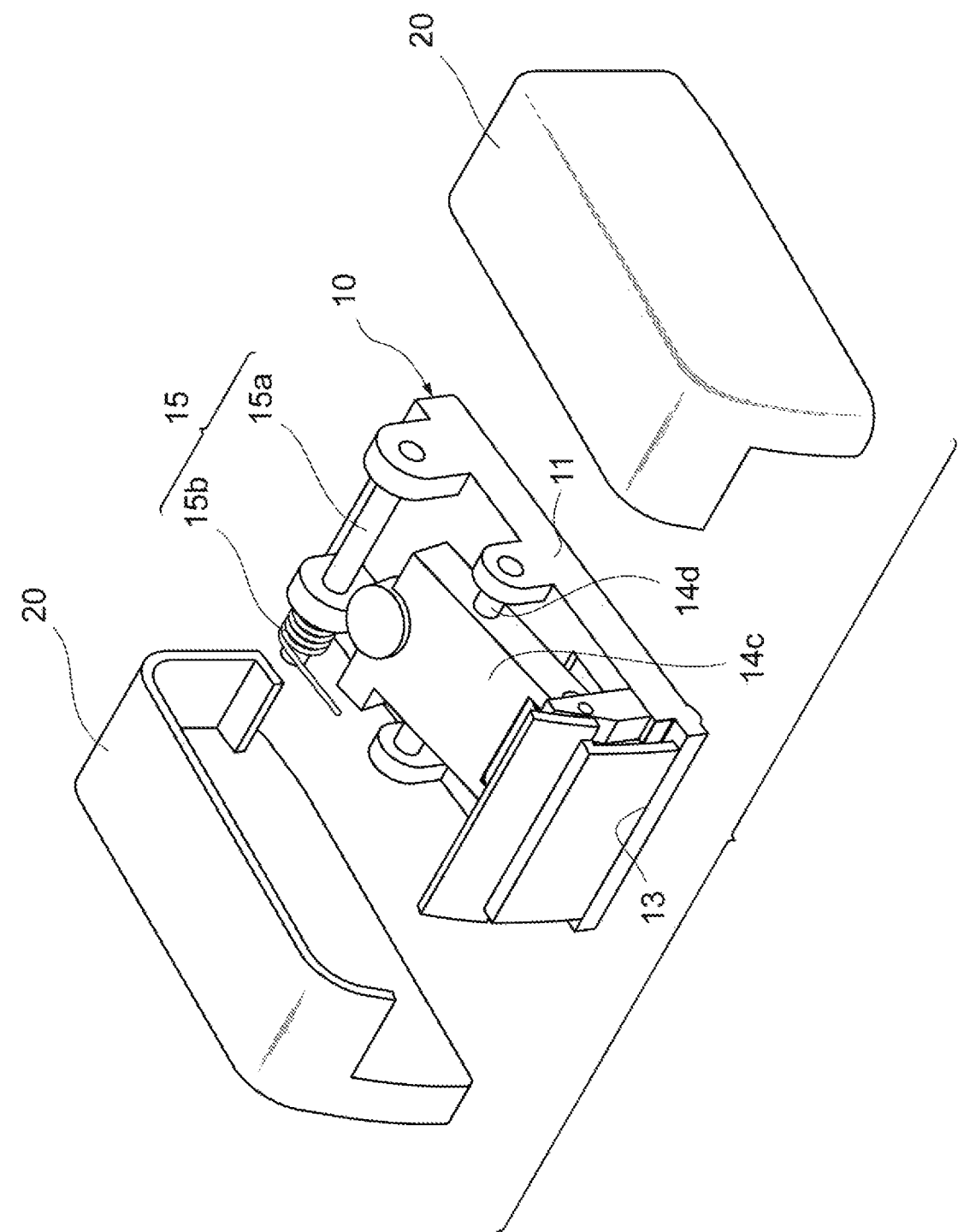
FIG. 5 is an exploded perspective view of the applicator according to the first embodiment.
Figure 6:
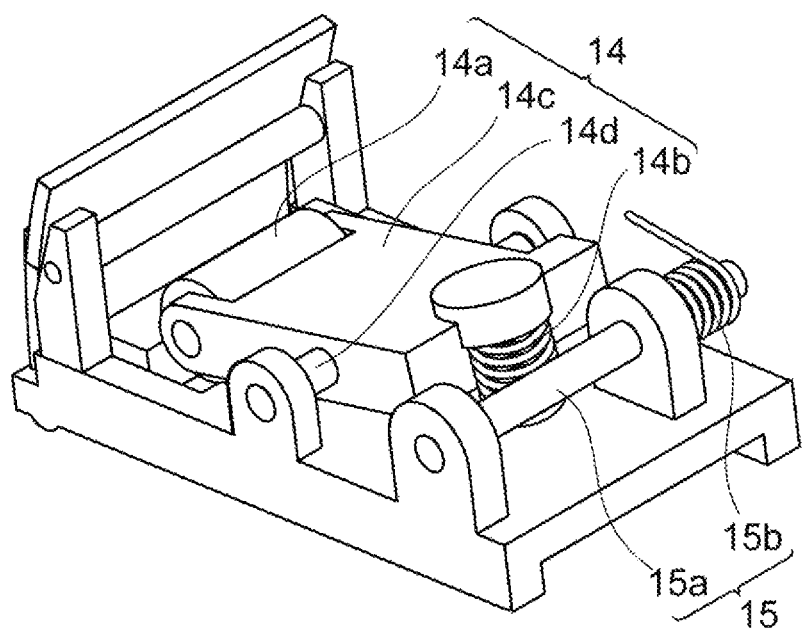
FIG. 6 is a perspective view of a movable plate of the applicator according to the first embodiment.

A structure of the applicator 1 will now be explained with reference to FIGS. 2 to 6. FIG. 2 is a perspective view from above, illustrating the applicator 1. FIG. 3 is a perspective view from below, illustrating the applicator 1. FIG. 4 is a schematic illustrating six sides of the applicator 1. FIG. 5 is an exploded perspective view of the applicator 1. FIG. 6 is a perspective view of a movable plate 10, which will be described later.

The entire applicator 1 has a cuboid shape and includes a movable plate 10 that becomes faced to the skin of a living body during the use, and a housing 20 that covers the movable plate 10. The movable plate 10 and the housing 20 are coupled to each other at one end by a coupling portion 15, and this mechanism allows the applicator 1 to move like a stapler. In this embodiment, the side of the housing 20 is defined as a top side of the applicator 1, and the side of the movable plate 10 is defined as a bottom side of the applicator 1. In this embodiment, the part of the housing 20 corresponding to the top surface of the applicator 1 is referred to as a top plate 21. The side on which the coupling portion 15 exists (the side on which the movable plate 10 and the housing 20 are coupled to each other) is defined as a rear side of the applicator 1, and the opposite side (the side on which the movable plate 10 and the housing 20 are brought closer to and away from each other around the coupling portion 15 serving as a rotational axis) is defined as a front side of the applicator 1. The direction perpendicularly intersecting with the up-and-down direction and the front-and-back direction of the applicator 1 is defined as a width direction of the applicator 1.

The movable plate 10 includes a bottom plate 11, a bending portion 12, a guide 13, a resisting portion 14, and the coupling portion 15.

A bottom plate 11 is a part that faces the skin of the living body during the use of the applicator 1. A thin and elongated protrusion 11a extending in the width direction is provided near the front end of the bottom surface of the bottom plate 11. By making a part of the bottom surface bulged toward the skin, this part presses the microneedle sheet 90 (sheet member) against the skin, such that the microneedle sheet 90 (sheet member) can be applied to the skin more reliably. The protrusion 11a is, however, not an essential element.

The bending portion 12 is a portion that bends the microneedle sheet 90. In this embodiment, the bending portion 12 is a thin cylindrical member extending in the width direction and provided to the front edge of a hole 11b formed on the bottom plate 11. This cylindrical member may be provided rotatably such that the microneedle sheet 90 can be advanced more smoothly, or may be configured not to rotate.

The guide 13 is a slit-shaped through-hole provided to the front end of the top surface of the bottom plate 11, extending in the width direction (although the guide 13 is illustrated with one line in the figures). The microneedle sheet 90 goes through the guide 13 into the applicator 1, advances in a manner following the top surface of the bottom plate 11, is bent by the bending portion 12 by approximately 180 degrees, and becomes applied to the skin.

The resisting portion 14 is a mechanism for applying resistance to the microneedle sheet 90 advancing toward the bending portion 12 and is provided to the top surface of the bottom plate 11. The purpose of providing the resisting portion 14 is to straighten slack of the microneedle sheet 90 by applying tensile force to the microneedle sheet 90 advancing toward the bending portion 12. The resisting portion 14 includes a roller 14a that is positioned between the guide 13 and the bending portion 12, a compression spring 14b extending in the up-and-down direction that is positioned behind the roller 14a, and a transmission plate 14c that transmits the elastic force of the compression spring 14b to the roller 14a. The front end of the transmission plate 14c is formed as a rotational shaft of the roller 14a, and the roller 14a is integrated with the transmission plate 14c via the shaft. One end of the compression spring 14b is mounted on the top surface of the bottom plate 11, and the other end of the compression spring 14b is compressed by the rear end of the transmission plate 14c. A shaft member 14d extending in the width direction is provided to the center of the transmission plate 14c, and the shaft member 14d is fixed to the bottom plate 11, thereby integrating the resisting portion 14 with the bottom plate 11. The elastic force of the compression spring 14b is transmitted to the roller 14a via the transmission plate 14c and causes the roller 14a to be pressed against the bottom plate 11. In other words, the compression spring 14b provides elastic force for pressing the roller 14a against the bottom plate 11. The roller 14a is one example of a pressing member, and the compression spring 14b is one example of an elastic member.

The microneedle sheet 90 having entered the applicator 1 through the guide 13 is passed between the bottom plate 11 and the roller 14a, and advances toward the bending portion 12. The roller 14a may be provided rotatably so as to move the microneedle sheet 90 forward smoothly while applying resistance, such as rolling friction and sliding friction, to the microneedle sheet 90. The rotation of the roller 14a is, however, not essential. Because the roller 14a is pressed against the bottom plate 11 by the elastic force of the compression spring 14b, the microneedle sheet 90 becomes nipped between the bottom plate 11 and the roller 14a. If the elastic force of the compression spring 14b is too strong, it becomes harder to insert the microneedle sheet 90 between the bottom plate 11 and the roller 14a, or for the microneedle sheet 90 to be carried toward the bending portion 12. By contrast, if the elastic force is too weak, the microneedle sheet 90 may become loosened, and the microneedle sheet 90 may be prevented from being applied to the skin appropriately (e.g., the microneedles 92 may fail to rise sufficiently). The structure or the elastic force of the compression spring 14b may be designed in any manner as long as the microneedle sheet 90 is stretched without any slack, and a user can easily operate the applicator 1.

The coupling portion 15 is a structure for coupling the housing 20 and the movable plate 10. The coupling portion 15 is provided with a shaft member 15a extending in the width direction, and a torsion spring 15b attached to one end of the shaft member 15a. The housing 20 and the movable plate 10 are integrated by the shaft member 15a, and a user can bring the front ends of the housing 20 and the movable plate 10 closer to and away from each other, around the shaft member 15a serving as the rotational axis. The elastic force of the torsion spring 15b acts in a direction bringing the front end of the housing 20 away from the front end of the movable plate 10. The torsion spring 15b is one example of the elastic member.

In this embodiment, the state in which no external force is applied to the applicator 1 and thus the front end of the housing 20 and the front end of the movable plate 10 are separated from each other is referred to as a "non-pressed state". This non-pressed state is also a state in which the top plate 21 is not moved (e.g., not pressed) toward the bottom plate 11. The non-pressed state can also be said as a natural state of the applicator 1. The state in which external force is applied to the housing 20 or the movable plate 10, and the front end of the housing 20 and the front end of the movable plate 10 are near to each other is referred to as a "pressed state". When a user moves (e.g., presses) the top plate 21 (or the housing 20) while the applicator 1 is placed on the skin, the front end of the housing 20 moves closer to the movable plate 10. This state is the pressed state. The structure or the elastic force of the torsion spring 15b may be designed considering appropriate application of a sheet member such as the microneedle sheet 90 to the skin.

The material with which the applicator 1 is fabricated is not limited to any particular material. An example of the material of the housing 20 and the movable plate 10 includes plastic such as acrylic resin, but a metal or another type of resin may also be used. The material of the bending portion 12 may be a metal, plastic such as acrylic resin, or another type of resin.

The size of the applicator 1 may be decided based on any criteria. For example, the width of the applicator 1 may be decided based on the width of the microneedle sheet 90. The total length of the applicator 1 (the length in the front-and-back direction) may be decided based on the operability.

Figure 7:
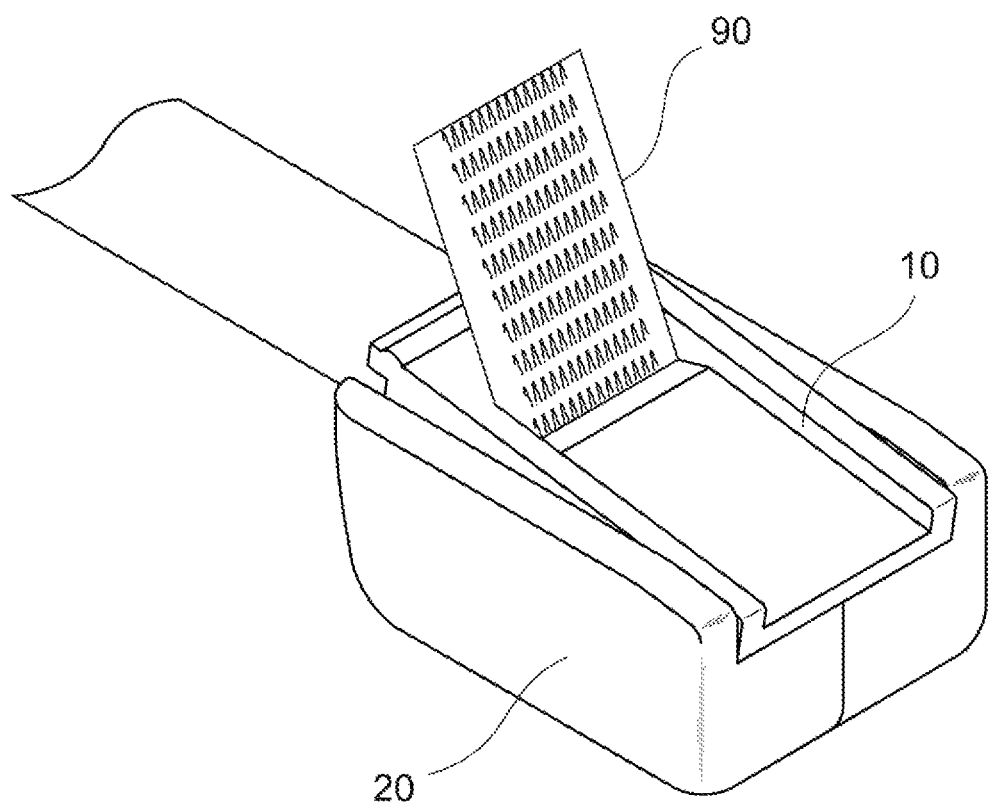
FIG. 7 shows how the applicator according to the first embodiment is used.
Figure 8:
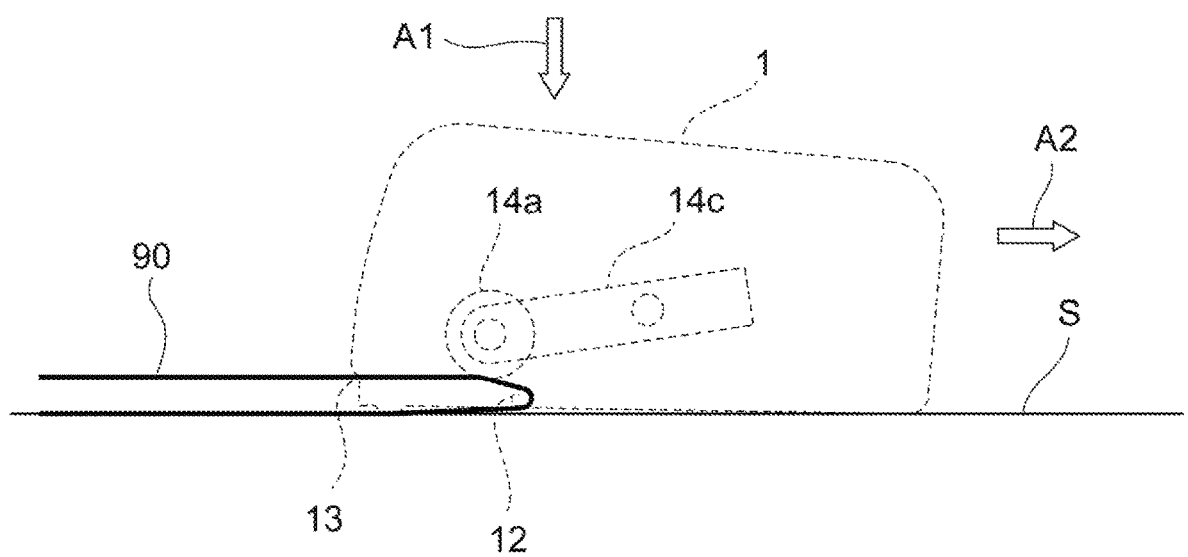
FIG. 8 shoes how the applicator according to the first embodiment is used.
Figure 9:
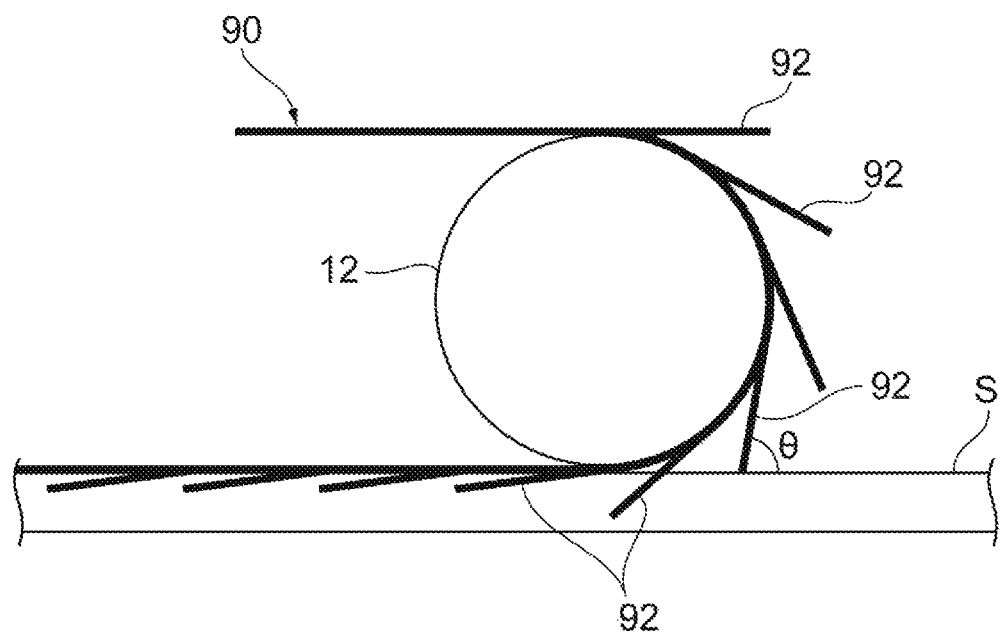
FIG. 9 schematically shows an example of puncture.

A usage of the applicator 1 and the microneedle sheet 90 will now be explained with reference to FIGS. 7 to 9. FIGS. 7 and 8 show how the applicator 1 is used. FIG. 9 schematically shows an example of puncture. In FIG. 8, in order to facilitate understanding of how the microneedle sheet 90 is set to the applicator 1, the microneedle sheet 90 is illustrated with a solid line, and the applicator 1 is illustrated with a dotted line.

To begin with, as illustrated in FIG. 7, a user sets the microneedle sheet 90 to the applicator 1. Specifically, a user passes one end of the microneedle sheet 90 through the hole 11b of the bottom plate 11 into the guide 13 or passes the one end through the guide 13 into the hole 11b of the bottom plate 11. The user then bends the microneedle sheet 90 near the bending portion 12. The direction to which the tips of the microneedles 92 point matches the direction from the guide 13 toward the bending portion 12.

The user then places the applicator 1 on the skin S (more specifically, on the region to which the active portion is to be applied). Merely by placing the applicator 1 on the skin S, the applicator 1 is still in the non-pressed state (natural state).

An adhesive may be applied to one end of the microneedle sheet 90 (the end that is brought into contact with the skin S at the beginning) such that any subsequent operations of the applicator 1 do not move the microneedle sheet 90 on the skin S. Alternatively, the user may fix the one end of the microneedle sheet 90 on the skin S using a finger or an adhesive tape, for example.

The user then moves the applicator 1 backward (in the direction indicated by the arrow A2) while moving the top plate 21 (or the housing 20) toward the bottom plate 11 (e.g., while pressing the top plate 21 in the direction indicated by the arrow A1), as illustrated in FIG. 8. This operation causes the microneedle sheet 90 to be pulled into the applicator 1 via the guide 13, to pass through the resisting portion 14 (more specifically the roller 14a), and to reach the bending portion 12. The microneedle sheet 90 is then bent by the bending portion 12 by approximately 180 degrees (reversed). The microneedles 92 that are positioned in the bent portion then rise from the principle surface 91, as illustrated in FIG. 9. The raised microneedles 92 then puncture the skin S. One row of the microneedles 92 in the width direction of the microneedle sheet 90 is raised at once between the applicator 1 and the skin S. As a matter of course, the angle formed by the raised microneedles 92 and the principle surface 91 is greater than 0 degrees and less than 180 degrees. As illustrated in FIG. 9, the puncture angle θ at which the microneedles 92 having been raised from the principle surface 91 puncture the skin (the angle formed by the microneedles 92 and the skin S) is also greater than 0 degrees and less than 180 degrees. The lower limit of the puncture angle may be 20 degrees, 34 degrees, or 40 degrees, and the upper limit of the angle may be 160 degrees, 140 degrees, or 100 degrees.

When the user moves the applicator 1 by a desirable distance, the microneedles 92 within the range of that distance puncture the skin. Therefore, the user can administer a desirable amount of active ingredient by adjusting the area to which the microneedle sheet 90 is applied. The user may remove the microneedle sheet 90 immediately or keep the microneedle sheet 90 applied to the skin S for a predetermined length of time.

As mentioned earlier, the applicator 1 may also be used in the application of a patch. The user sets a patch to the applicator 1, in the same manner as for the microneedle sheet 90, with the adhesive layer facing upwardly. The user then moves back the applicator 1 while pressing down the top plate 21 toward the bottom plate 11. This operation causes the adhesive layer (the active surface of the patch) to be bent, with its curve facing outwardly, around the bending portion 12, and to cause the liner to be removed and to cause the patch to stick to the skin.

Second Embodiment

Figure 10:
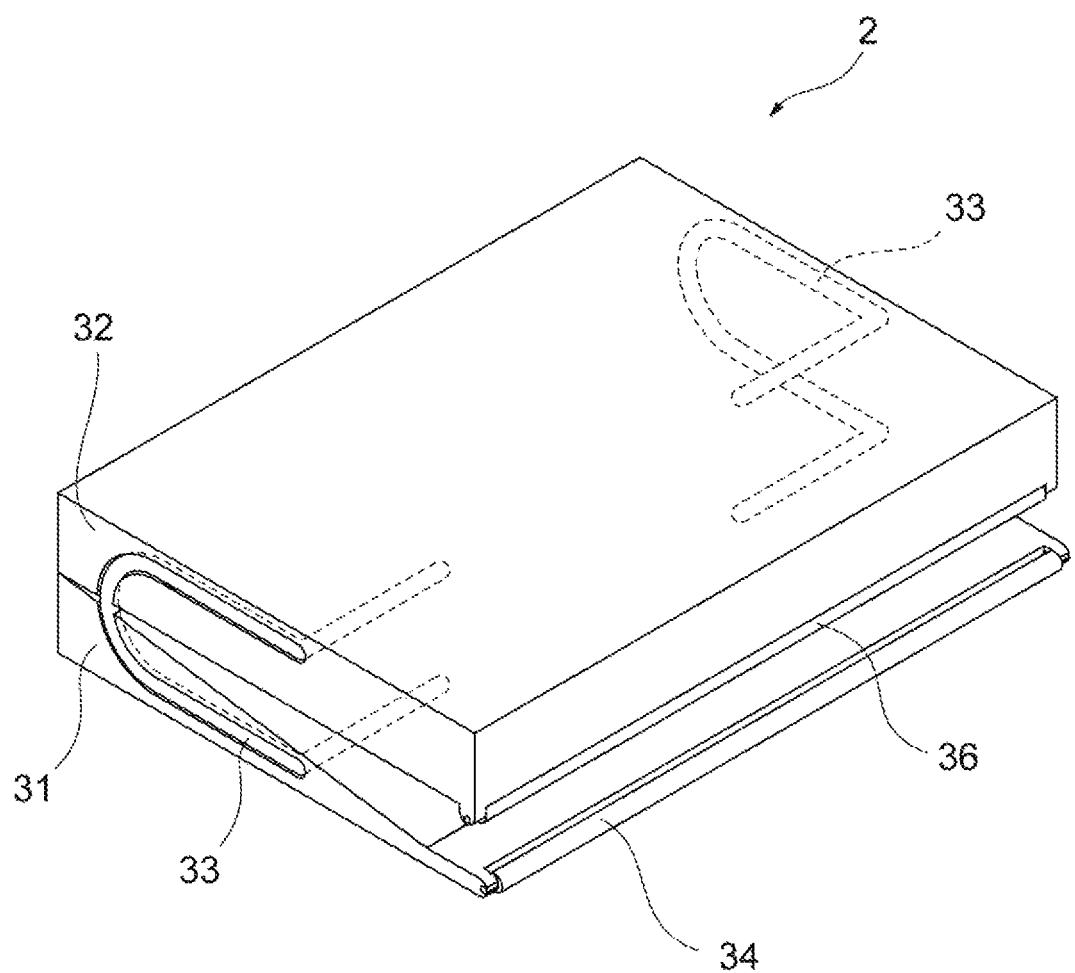
FIG. 10 is a perspective view of the applicator according to the second embodiment.
Figure 11:
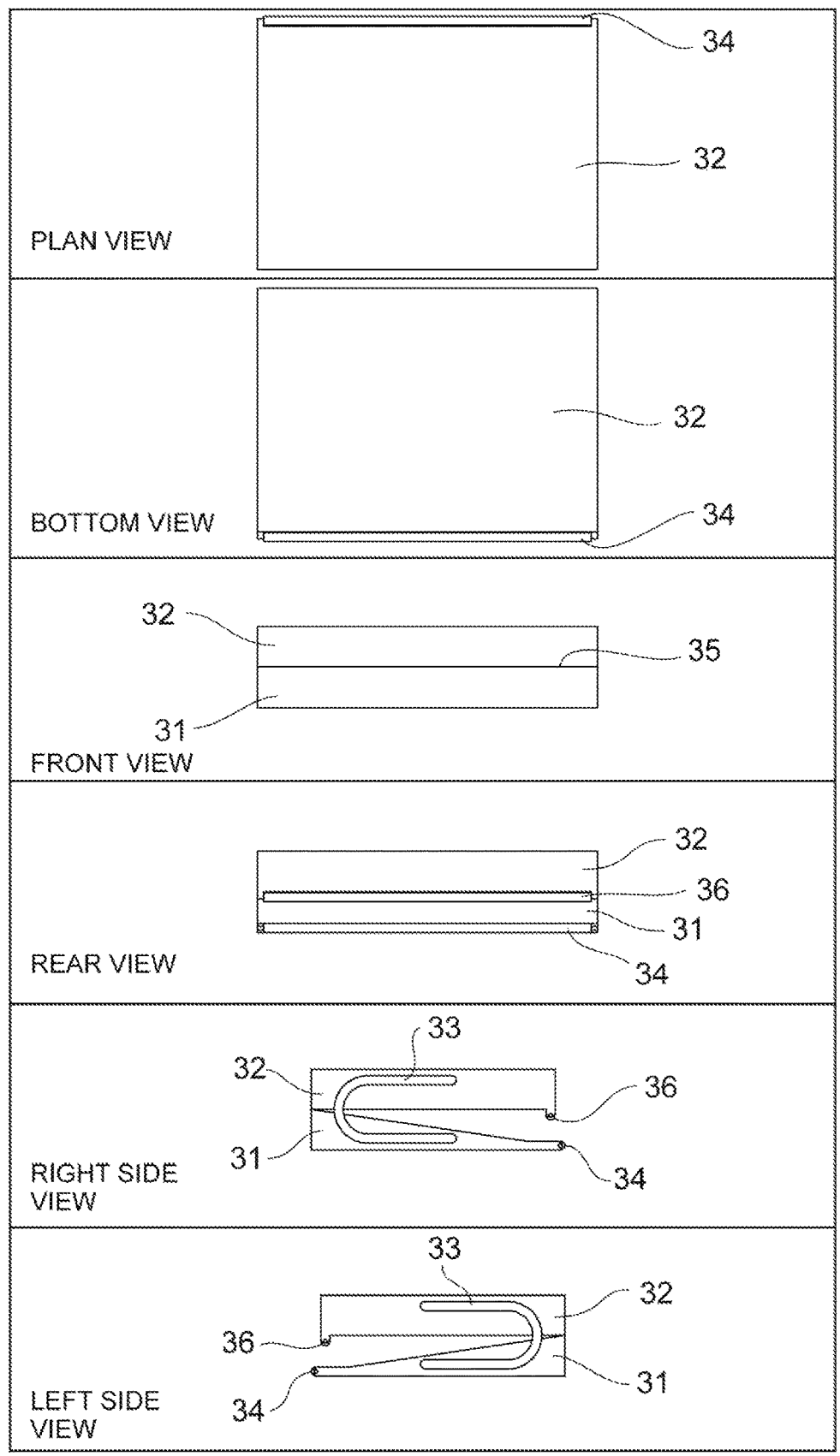
FIG. 11 is a schematic illustrating six sides of the applicator according to the second embodiment.

A structure of an applicator 2 according to a second embodiment will now be explained using FIGS. 10 and 11. FIG. 10 is a perspective view of the applicator 2. FIG. 11 is a schematic illustrating six sides of the applicator 2. Also in this embodiment, a microneedle sheet is presented as an example of the sheet member.

The applicator 2 includes a bottom plate 31 and a top plate 32 both of which are flat. The applicator 2 is formed by the two plates 31 and 32 being coupled to each other at one end via torsion springs 33, with the two plates 31 and 32 placed on top of each other. The bottom plate 31 is a plate member that becomes faced to the skin of the living body during the use, and the top plate 32 is a plate member that faces the bottom plate 31. In this embodiment, the side of the top plate 32 is defined as a top side of the applicator 2, and the side of the bottom plate 31 is defined as a bottom side of the applicator 2. The side on which the torsion springs 33 exists (the side on which the bottom plate 31 and the top plate 32 are coupled to each other) is defined as a front side of the applicator 2, and the opposite side is defined as a rear side of the applicator 2. The direction perpendicularly intersecting with the up-and-down direction and the front-and-back direction of the applicator 2 is defined as the width direction of the applicator 2. The cross-section of the bottom plate 31 across the front-and-back direction has a substantially right triangular shape that is thin and elongated, and becoming narrower in a direction from the front side toward the rear side. By contrast, the section of the top plate 32 across the front-and-back direction has a thin and elongated rectangular shape.

The user can bring the rear ends of the bottom plate 31 and the top plate 32 closer to and away from each other around the area near the torsion springs 33 serving as a rotational axis. The elastic forces of the torsion springs 33 act in a direction bringing the bottom plate 31 away from the top plate 32.

In this embodiment, the state in which no external force is applied to the applicator 2 and thus the rear end of the bottom plate 31 and the rear end of the top plate 32 are separated from each other is referred to as a "non-pressed state". This non-pressed state is also a state in which the top plate 32 is not moved (e.g., not pressed) toward the bottom plate 31. The non-pressed state can also be said as a natural state of the applicator 2. The state in which external force is applied to the bottom plate 31 or the top plate 32, and the rear end of the bottom plate 31 and the rear end of the top plate 32 are near to each other is referred to as the "pressed state". When a user moves (e.g., presses) the top plate 32 while the applicator 2 is placed on the skin, the rear end of the top plate 32 moves closer to the bottom plate 31. This state is the pressed state. The structure or the elastic force of the torsion springs 33 may be designed considering how a sheet member, such as the microneedle sheet 90, can be applied appropriately to the skin. The torsion springs 33 are one example of the elastic member.

A bending portion 34 for bending the microneedle sheet 90 is provided to the rear end of the bottom plate 31. This bending portion 34 is a thin cylindrical member that is provided in a manner extending in the width direction. This cylindrical member may be provided rotatably such that the microneedle sheet 90 can be advanced more smoothly, or may be configured not to rotate.

A guide 35 for guiding the microneedle sheet 90 to the bending portion 34 is provided to the front end of the applicator 2. The guide 35 is a slit-shaped through-hole formed by the front end of the top surface of the bottom plate 31 and the front end of the bottom surface of the top plate 32 (although the guide 35 is illustrated with one line in the figures). In the non-pressed state (the natural state of the applicator 2), the guide 35 is closed, but, in the pressed state, becomes opened to a degree allowing the microneedle sheet 90 to pass through. In the non-pressed state, the guide 35 prevents the microneedle sheet 90 from advancing toward the bending portion 34. The microneedle sheet 90 goes through the guide 35 into the applicator 2, advances along the top surface of the bottom plate 31, bends around the bending portion 34 by approximately 180 degrees, and becomes applied to the skin.

A resisting portion 36 for applying resistance to the microneedle sheet 90 advancing toward the bending portion 34 is provided to the rear end of the bottom surface of the top plate 32. The resisting portion 36 is a thin cylindrical member that is provided in a manner extending in the width direction. This cylindrical member may be provided rotatably so as to move the microneedle sheet 90 forward smoothly while applying resistance to the microneedle sheet 90. The rotation of the resisting portion 36 is, however, not essential. The purpose of providing the resisting portion 36 is to straighten slack of the microneedle sheet 90 by applying tensile force to the microneedle sheet 90 advancing toward the bending portion 34. The resisting portion 36 is positioned on the front side of the bending portion 34. If the applicator 2 is pulled back along the skin in the pressed state, the microneedle sheet 90 can move through the guide 35 into the applicator 2, but the microneedle sheet 90 advancing toward the bending portion 34 becomes nipped between the resisting portion 36 and the bottom plate 31.

The material of which the applicator 2 is made is not limited to any particular material, in the same manner as in the first embodiment, and the size of the applicator 2 may be decided based on any criteria.

Figure 12:
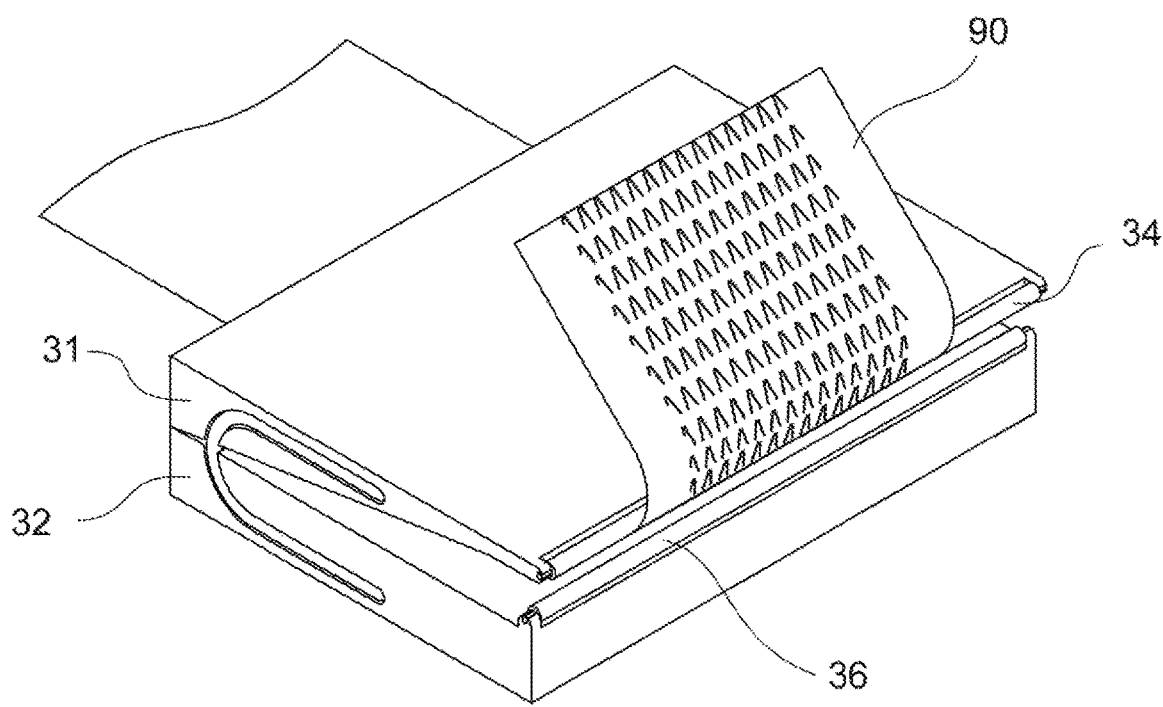
FIG. 12 shows how the applicator according to the second embodiment is used.
Figure 13:
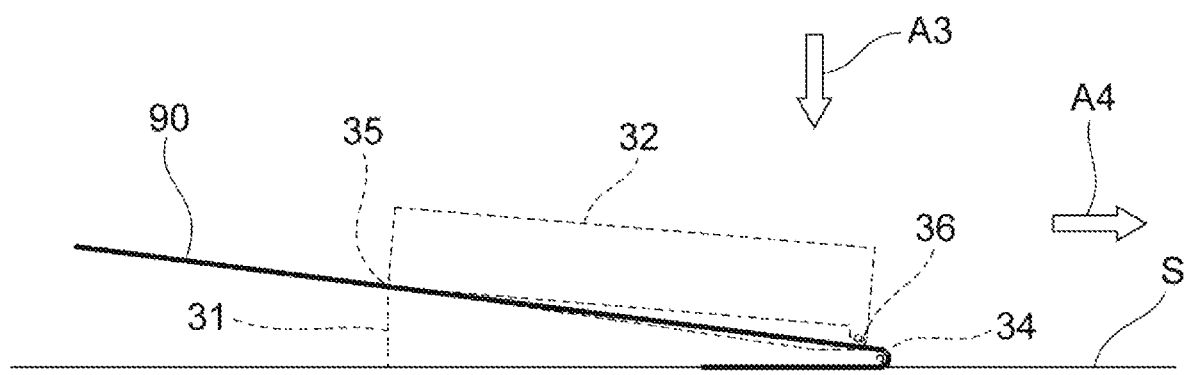
FIG. 13 shows how the applicator according to the second embodiment is used.

A usage of the applicator 2 and the microneedle sheet 90 will now be explained using FIGS. 12 and 13. FIGS. 12 and 13 show how the applicator 2 is used. In FIG. 13, in order to facilitate understanding of how the microneedle sheet 90 is set to the applicator 2, the microneedle sheet 90 is illustrated with a solid line, and the applicator 2 is illustrated with a dotted line.

To begin with, as illustrated in FIG. 12, a user sets the microneedle sheet 90 to the applicator 2. Specifically, the user opens the guide 35 by pressing the top plate 32 toward the bottom plate 31, and passes one end of the microneedle sheet 90 from the rear side of the applicator 2 into the guide 35, or passes the one end from the guide 35 into the rear side of the applicator 2. The user then bends the microneedle sheet 90 near the bending portion 34. The direction to which the tips of the microneedles 92 point matches the direction from the guide 35 toward the bending portion 34.

The user then places the applicator 2 on the skin S (more specifically, on the region to which the active portion is to be applied). An adhesive may be applied to one end of the microneedle sheet 90 such that any subsequent operations of the applicator 2 do not move the microneedle sheet 90 on the skin S, in the same manner as in the first embodiment. The user may also fix one end of the microneedle sheet 90 on the skin S using a finger or an adhesive tape, in the same manner as in the first embodiment.

The user then moves the applicator 2 backward (in the direction indicated by the arrow A4) while moving the top plate 32 toward the bottom plate 31 (e.g., while pressing the top plate 32 in the direction indicated by the arrow A3), as illustrated in FIG. 13. This operation causes the microneedle sheet 90 to be pulled into the applicator 2 via the guide 35, to pass through the resisting portion 36, and to reach the bending portion 34. The microneedle sheet 90 is then bent by the bending portion 34 by approximately 180 degrees (reversed). The microneedles 92 that are positioned in the bent portion then rise from the principle surface 91, and the raised microneedles 92 then puncture the skin S (see FIG. 9), in the same manner as in the first embodiment. The way in which the microneedles 92 are raised and the puncture angle $\theta$ at which the microneedles 92 puncture the skin S are the same as those according to the first embodiment.

When the user moves the applicator 2 by a desirable distance, the microneedles 92 within the range of that distance punctures the skin. Therefore, the user can administer a desirable amount of active ingredient by adjusting the area to which the microneedle sheet 90 is applied. The user may remove the microneedle sheet 90 immediately or keep the microneedle sheet 90 applied to the skin S for a predetermined length of time. These are also the same as those in the first embodiment.

The applicator 2 may be used in the application of a patch. The user sets a patch to the applicator 2, in the same manner as for the microneedle sheet 90, with the adhesive layer facing upwardly. The user then pulls back the applicator 2 while pressing the top plate 32 toward the bottom plate 31. This operation causes the adhesive layer (the active surface of the patch) to be bent, with its curve facing outwardly, around the bending portion 34, and to cause the liner to be removed and to cause the patch to stick to the skin.

Third Embodiment

Figure 14:
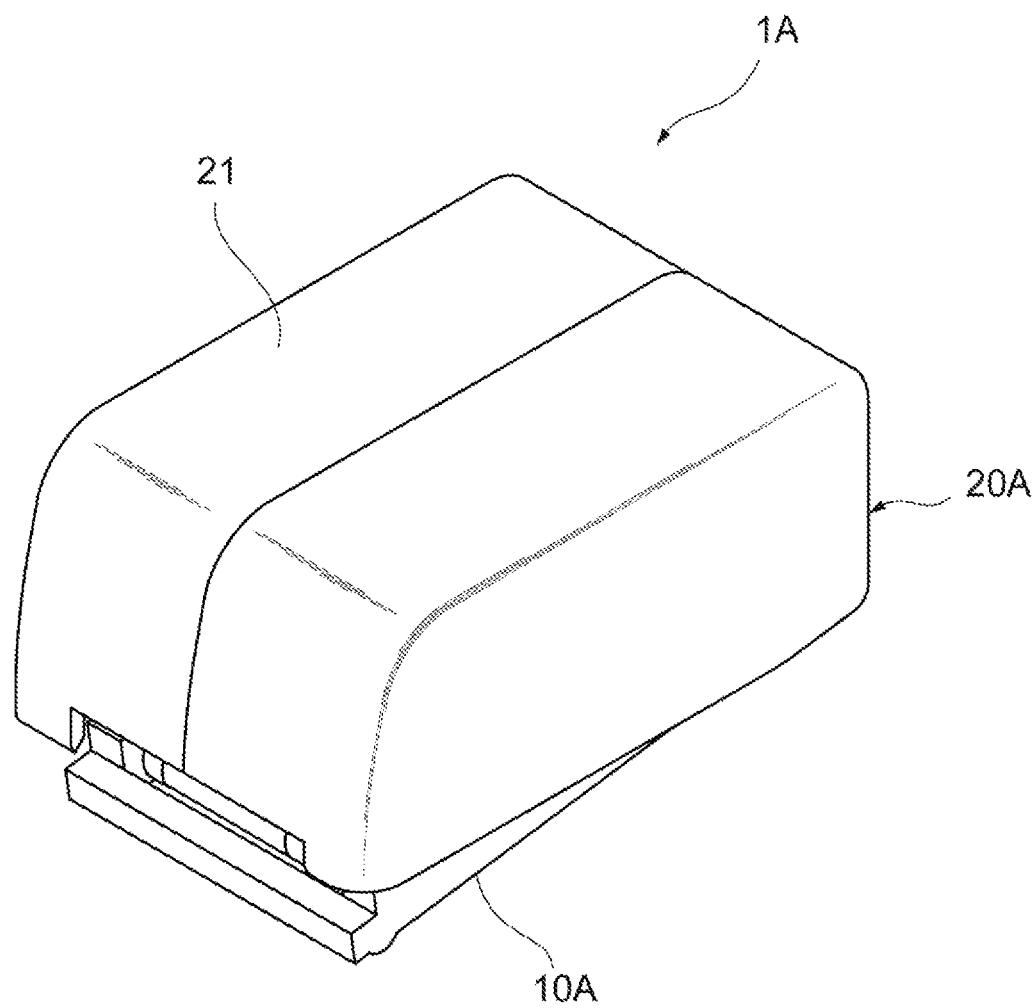
FIG. 14 is a perspective view from above, illustrating an applicator according to a third embodiment.
Figure 15:
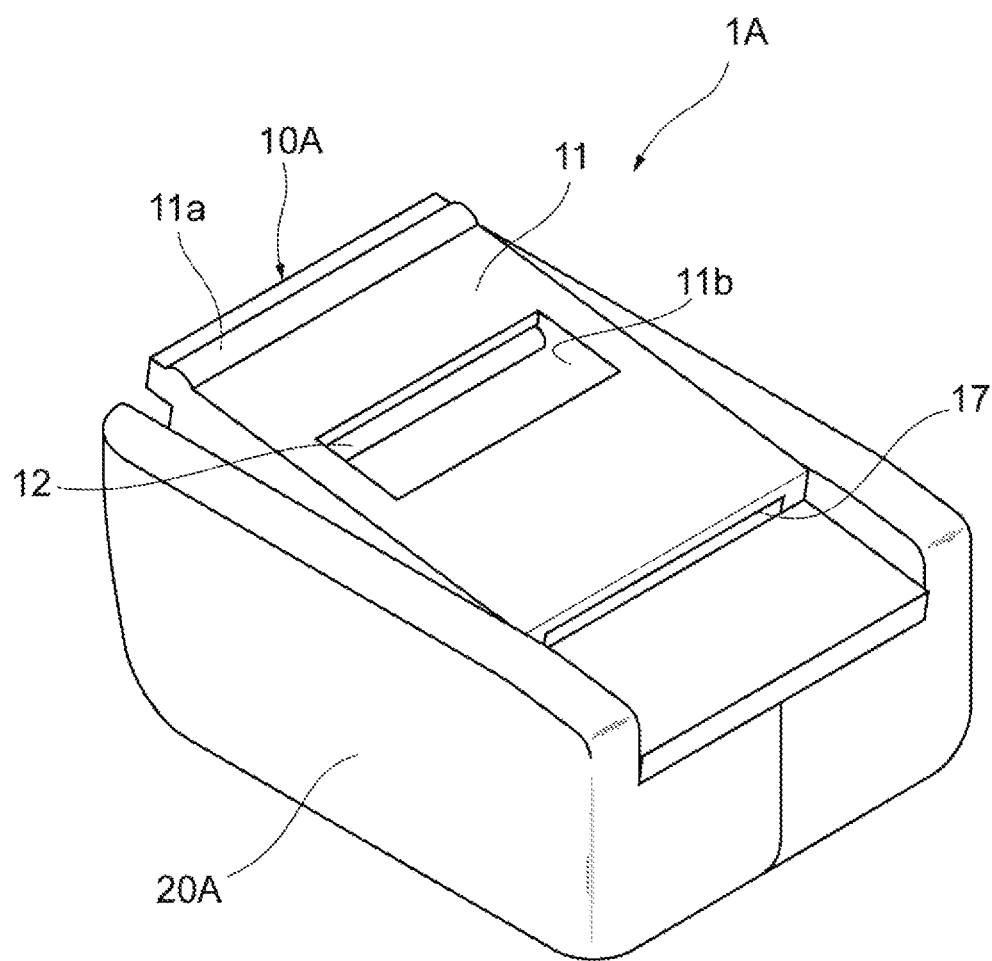
FIG. 15 is a perspective view from below, illustrating the applicator according to the third embodiment.
Figure 16:
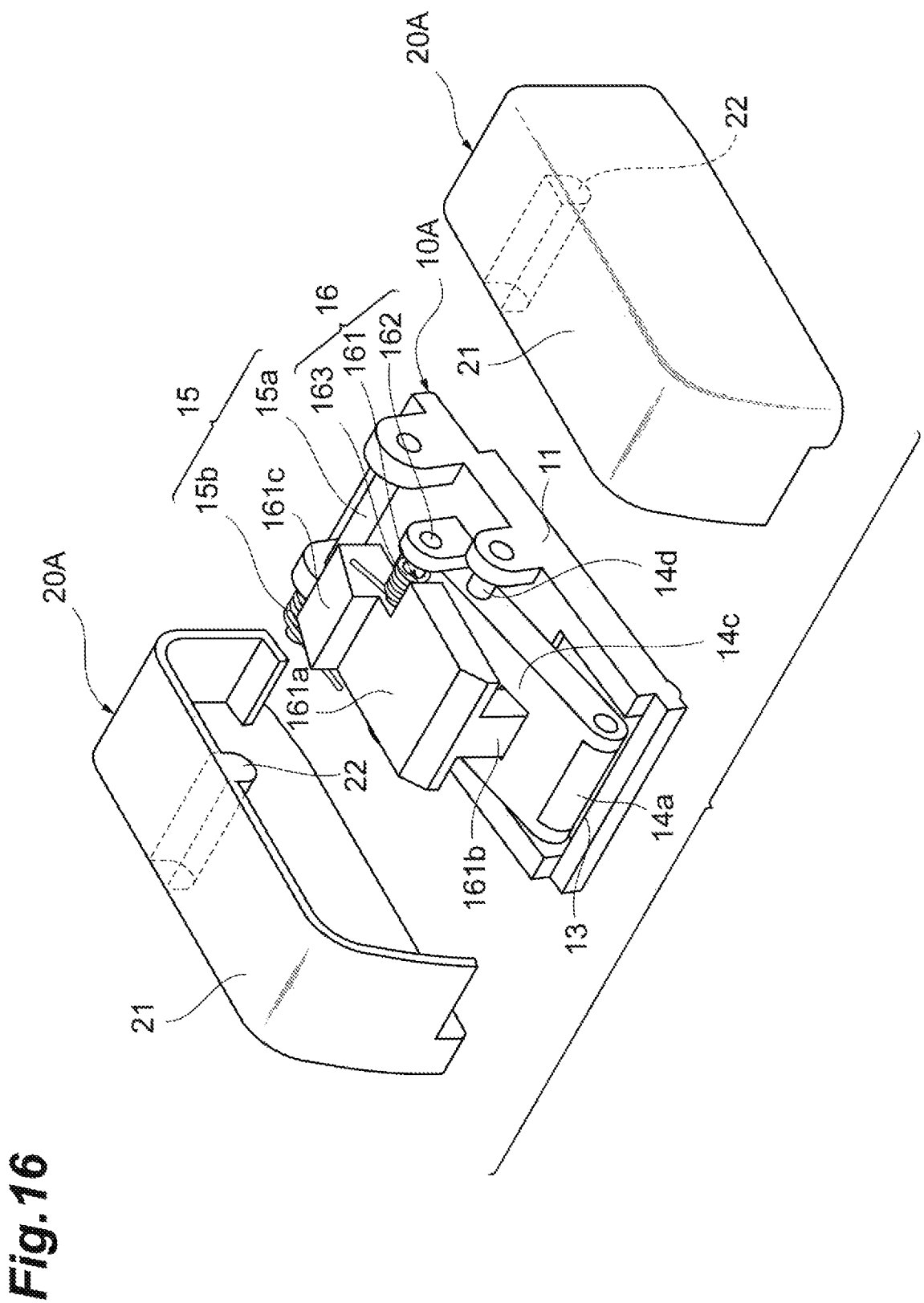
FIG. 16 is an exploded perspective view of the applicator according to the third embodiment.

The applicator according to the first embodiment that operates in a stapler-like motion may be configured to prevent the sheet member from advancing toward the bending portion in the non-pressed state. This modification will now be explained as a third embodiment using FIGS. 14 to 17. FIG. 14 is a perspective view from above, illustrating an applicator 1A according to the third embodiment. FIG. 15 is a perspective view from below, illustrating the applicator 1A. FIG. 16 is an exploded perspective view of the applicator 1A. FIG. 17 shows how the applicator 1A is used, particularly how a stopper moves. In the explanation hereunder, the points that are different from those in the first embodiment will be mainly explained, and the structures and the functions that are the same as equivalent to those of the first embodiment will be briefly explained, or the explanations thereof will be omitted.

The entire applicator 1A has a cuboid shape and includes a movable plate 10A that becomes faced to the skin of a living body during the use, and a housing 20A that covers the movable plate 10A. The movable plate 10A and the housing 20A are coupled to each other at one end by the coupling portion 15, and this mechanism allows the applicator 1A to move like a stapler. In this embodiment, the side of housing 20A is defined as a top side of the applicator 1A, and the side of the movable plate 10A is defined as a bottom side of the applicator 1A. The part of the housing 20A corresponding to the top surface of the applicator 1A is referred to as the top plate 21. The side on which the coupling portion 15 exists (the side on which the movable plate 10A and the housing 20A are coupled to each other) is defined as a rear side of the applicator 1A, and the opposite side (the side on which the movable plate 10A and the housing 20A are brought closer to and away from each other around the coupling portion 15 serving as a rotational axis) is defined as a front side of the applicator 1A. The direction perpendicularly intersecting with the up-and-down direction and the front-and-back direction of the applicator 1A is defined as the width direction of the applicator 1A.

The movable plate 10A includes a stopper 16 and a discharge port 17, in addition to the bottom plate 11, the bending portion 12, the guide 13, the resisting portion 14, and the coupling portion 15.

The structures of the bottom plate 11, the bending portion 12, the guide 13, the resisting portion 14, and the coupling portion 15 are the same as or equivalent to those of the first embodiment. The bottom plate 11 is a part that faces the skin of the living body during the use of the applicator 1A. The thin and elongated protrusion 11a may be provided near the front end of the bottom surface of the bottom plate 11. The bending portion 12 is a part that bends the microneedle sheet 90, and is a cylindrical member provided to the front edge of the hole 11b formed on the bottom plate 11, extending in the width direction. The guide 13 is a slit-shaped through-hole provided to the front end of the top surface of the bottom plate 11, extending in the width direction. The microneedle sheet 90 goes through the guide 13 into the applicator 1A. The resisting portion 14 is a mechanism for applying resistance to the microneedle sheet 90 advancing toward the bending portion 12. The resisting portion 14 includes, in the same manner as in the first embodiment, the roller 14a, the compression spring 14b (not illustrated), the transmission plate 14c, and the shaft member 14d. The coupling portion 15 is a structure for coupling the housing 20A and the movable plate 10A, and includes the shaft member 15a and the torsion spring 15b.

Also in this embodiment, the state in which no external force is applied to the applicator 1A and thus the front end of the housing 20A and the front end of the movable plate 10A are separated from each other is referred to as a "non-pressed state", and the state in which external force is applied to the housing 20A or the movable plate 10A, and the front end of the housing 20A and the front end of the movable plate 10A are near to each other is referred to as a "pressed state".

The stopper 16 is an element that guides the sheet member to the bending portion 12 in the pressed state, and prevents, in the non-pressed state, the sheet member from advancing toward the bending portion 12. The stopper 16 is provided to the top surface of the bottom plate 11. The stopper 16 includes a stopper body 161, entire body of which has an L shape, and a shaft member 162 attached to the stopper body 161 in a manner penetrating the stopper body 161 in the width direction, and a torsion spring 163 attached to one end of the shaft member 162. The stopper body 161 has a horizontal portion 161a extending along the bottom plate 11 in the front-and-back direction, and a foot 161b extending downwardly from the front end of the horizontal portion 161a. In this embodiment, the transmission plate 14c has a hole corresponding to the foot 161b, and the stopper body 161 is arranged in such a manner that the foot 161b is passed through the transmission plate 14c. The tip (bottom end) of the foot 161b can be brought into contact with the top surface of the bottom plate 11. The rear end of the horizontal portion 161a (the section behind the shaft member 162) is formed in a manner bulging upwardly, and in the explanation hereunder, this portion is referred to as a bulge 161c. The shaft member 162 is fixed to the bottom plate 11, thereby integrating the stopper 16 with the bottom plate 11. The elastic force of the torsion spring 163 acts in the direction pressing the tip of the foot 161b against the bottom plate 11. The torsion spring 163 is one example of the elastic member.

The discharge port 17 is a slit-shaped through-hole provided behind the bottom plate 11, extending in the width direction. The discharge port 17 is a hole for discharging the liner 93 (see FIG. 17) removed from the microneedle sheet 90 to the outside of the applicator 1A. In this embodiment, the microneedle sheet 90 is provided in a manner protected with the liner 93.

A protrusion 22 extending in the width direction is provided to the ceiling of the housing 20A (inner side of the top plate 21). This protrusion 22 is provided at a position with which the bulge 161c of the stopper 16 can be brought into contact.

A usage of the applicator 1A and the microneedle sheet 90 and control of the advancement of the microneedle sheet 90 with the stopper 16 will now be explained with reference to FIG. 17. In FIG. 17, in order to illustrate the advancement of the microneedle sheet 90 and the liner 93 and the movement of the stopper 16 in an easy-to-understand fashion, the microneedle sheet 90, the liner 93, the stopper 16, and the protrusion 22 are illustrated with solid lines, and the applicator 1A is illustrated with a dotted line.

A user passes one end of the microneedle sheet 90 with a liner 93 through the hole 11b of the bottom plate 11 into the guide 13, or through the guide 13 into the hole 11b of the bottom plate 11. The direction to which the tips of the microneedles 92 point matches the direction from the guide 13 toward the bending portion 12. The user then removes the liner 93 from the microneedle sheet 90 near the bending portion 12 and bends the microneedle sheet 90. The leading end of the removed liner 93 then becomes positioned in front of the foot 161b.

The user then places the applicator 1A on the skin S (more specifically, on the region to which the active portion is to be applied). Merely by placing the applicator 1A on the skin S, the applicator 1A is still in the non-pressed state (natural state). In this non-pressed state, because the elastic force of the torsion spring 163 keeps the tip of the foot 161b of the stopper 16 pressed toward the bottom plate 11, the path to the discharge port 17 is closed by the stopper body 161 (more specifically, by the foot 161b). Therefore, the removed liner 93 is prevented from advancing into the discharge port 17. Because the removed liner 93 is still connected to the liner 93 on the remaining area that is still bonded to the microneedle sheet 90, the microneedle sheet 90 is, as a result, also prevented from advancing toward the bending portion 12.

The user then moves the top plate 21 (or the housing 20A) toward the bottom plate 11 (e.g., pushes in the direction indicated by the arrow A5). This operation causes the protrusion 22 of the housing 20A to abut against the bulge 161c of the stopper 16, and to lower the bulge 161c. The stopper body 161 then moves away from bottom plate 11 (more specifically, the foot 161b moves away from the bottom plate 11) by rotating around the shaft member 162, in a manner resisting against the elastic force of the torsion spring 163. As a result, because the path (the path to the discharge port 17) which has been closed is now open, the liner 93 is enabled to move freely. Therefore, as the user moves the applicator 1A to the rear side of the applicator 1A (in the direction indicated by the arrow A6) while maintaining the pressed state, the microneedle sheet 90 is pulled into the applicator 1A through the guide 13, reaches the bending portion 12, and is bent by the bending portion 12 by approximately 180 degrees (reversed). The microneedles 92 that are positioned in the bent portion are then raised from the principle surface 91, and the raised microneedles 92 then puncture the skin S. The liner 93 removed from the microneedle sheet 90 by the bending portion 12 is discharged outside of the applicator 1A via the discharge port 17.

When the user stops pressing the top plate 21 after moving back the applicator 1A while maintaining the pressed state, the foot 161b having been kept separated from the bottom plate 11 is pressed against the bottom plate 11 again by the elastic force of the torsion spring 163. In the non-pressed state, the liner 93 having been advanced toward the discharge port 17 becomes nipped between the bottom plate 11 and the foot 161b such that the liner 93 is prevented from advancing any further, and thus the microneedle sheet 90 is prevented from advancing toward the bending portion 12. In this manner, with the use of the applicator 1A, the microneedle sheet 90 can be applied to the skin only when the user applies pressing force at a certain level or higher to the top plate 21 (or the housing 20A).

The applicator 1A can also be used in the application of a patch, and in the same manner as described in the first embodiment.

As described above, an applicator according to one aspect of the present invention is an applicator for applying a sheet member to skin, the applicator including: a bottom plate facing the skin; a top plate facing the bottom plate and configured to be pressed down toward the bottom plate; and a bending portion configured to apply the sheet member to the skin by bending the sheet member having advanced thereto in a pressed state in which the top plate has been moved toward the bottom plate.

According to this aspect, the bending portion is configured to apply the sheet member to the skin by bending the sheet member having advanced thereto in a configuration in which the applicator (more specifically, the top plate) has been moved toward the skin. With this mechanism, the pressing force at a certain level or higher is applied to the sheet member when the sheet member is applied to the skin. Therefore, whoever the person using the applicator is, the sheet member can be appropriately applied to the skin. This means that the reproducibility of the application of a sheet member can be improved. For example, in the application of a patch, the adhesive layer can be applied firmly to the skin without causing the patch to wrinkle. Furthermore, in the application of a microneedle sheet, the applicator can raise the microneedles from the principle surface of the sheet as the sheet becomes bent, such that the microneedles can be inserted more firmly into the skin.

In the application of a microneedle sheet, the applicator according to one aspect of the present invention allows the microneedles to puncture the skin by raising the microneedles, and pushing the microneedles into the skin, instead of by applying an impact onto the microneedle sheet. Therefore, an active ingredient can be administered to the recipient without causing any fear in the recipient.

An applicator according to another aspect may further include a guide configured to guide the sheet member toward the bending portion in the pressed state, and to prevent advancement of the sheet member toward the bending portion in a non-pressed state in which the top plate has not been moved toward the bottom plate. With this configuration for preventing advancement of the sheet member without moving the top plate, it is possible to prevent any unintended advancement of the sheet member.

An applicator according to another aspect may further include a stopper configured to guide the sheet member toward the bending portion in the pressed state, and to prevent advancement of the sheet member toward the bending portion in a non-pressed state in which the top plate has not been moved toward the bottom plate. With this configuration for preventing advancement of the sheet member without moving the top plate, it is possible to prevent any unintended advancement of the sheet member.

In an applicator according to another aspect, the stopper may include a stopper body, and an elastic member providing elastic force for pressing the stopper body against the bottom plate, the top plate may include a protrusion enabled to be brought into contact with the stopper body, in the non-pressed state, advancement of the sheet member may be prevented by keeping the protrusion away from the stopper body such that the elastic force presses the stopper body against the bottom plate, and the protrusion may be brought into contact with the stopper body and the stopper is moved away from the bottom plate in a manner resisting against the elastic force in the pressed state, such that the sheet member is guided toward the bending portion. With this configuration using elastic force, it is possible to achieve a mechanism for preventing any unintended advancement of the sheet member more reliably using a simple structure.

An applicator according to another aspect may further include a resisting portion configured to apply resistance to the sheet member advancing toward the bending portion at least in the pressed state. By applying a resistance to the sheet member, the advancement of the sheet member can be kept constant, and the sheet member can be applied to the skin with constant force.

In an applicator according to another aspect, the resisting portion may be configured to nip the sheet member to apply resistance to the sheet member in the pressed state, and not to nip the sheet member in a non-pressed state in which the top plate has not been moved toward the bottom plate. With such a configuration, the resistance can be applied to the sheet member only when the sheet member is advancing toward the bending portion, that is, only when the sheet member is being applied to the skin.

In an applicator according to another aspect, the resisting portion may include: a pressing member; and an elastic member configured to provide elastic force for pressing the pressing member against the bottom plate, and the resisting portion may apply resistance to the sheet member by nipping the sheet member advancing toward the bending portion with the bottom plate and the pressing member. In this manner, by nipping the sheet member using the elastic force, the resistance applied to the sheet member can be kept constant.

An applicator according to another aspect may further include an elastic member configured to generate elastic force acting in a direction moving the bottom plate and the top plate away from each other. With this mechanism, the pressing force applied to the sheet member can be kept to a certain level or higher when the sheet member is applied to the skin. Therefore, whoever the person using the applicator is, the sheet member can be appropriately applied to the skin.

In an applicator according to another aspect, the sheet member may be a microneedle sheet having a plurality of microneedles provided in a manner laid along a principle surface of the sheet. With such a configuration, the applicator can raise the microneedles from the principle surface of the sheet, such that the microneedles can be inserted more firmly into the skin.

While the present invention is explained above in detail based on the embodiments thereof, the scope of the present invention is not limited to these embodiments, and various modifications of the present invention are still possible within the scope not deviating the spirit thereof.

As mentioned earlier, the sheet member is not limited to a microneedle sheet. The applicator according to one aspect of the present invention may be used for various types of sheet members, including a patch.

The guide 13 explained in the first embodiment may be configured, in the same manner as the guide 35 in the second embodiment, to remain closed in the non-pressed state (in the natural state of the applicator 1), and to become open to a degree allowing the sheet member to pass therethrough in the pressed state. In other words, the guide 13 may be designed to prevent the advancement of the sheet member toward the bending portion 12 in the non-pressed state.

In the applicator 2 according to the second embodiment, a protrusion may be provided to the bottom surface of the bottom plate 31, in the same manner as in the first embodiment.

In the embodiments described above, a cylindrical member is used as the bending portion, but the configuration of the bending portion is not limited, as long as the bending portion is capable of bending the sheet member and raise the microneedles. For example, one end of a flat plate may serve as the bending portion.

In the embodiments described above, the sheet member is set to the applicator by inserting the sheet member from the front side (or the rear side) toward the rear side (or the front side), but the applicator may also be designed in such a manner that the sheet member can be inserted from a side of the applicator.

The configurations of the guide and the resisting portion are not limited to those described in the embodiments. Furthermore, the guide and the resisting portion may both be omitted. For example, the guide 13 may serve as the resisting portion.

REFERENCE SIGNS LIST

1 . . . applicator, 10 . . . movable plate, 11 . . . bottom plate, 12 . . . bending portion, 13 . . . guide, 14 . . . resisting portion, 14a . . . roller (pressing member), 14b . . . compression spring (elastic member), 20 . . . housing, 21 . . . top plate, 2 . . . applicator, 31 . . . bottom plate, 32 . . . top plate, 34 . . . bending portion, 35 . . . guide, 36 . . . resisting portion, 22 . . . protrusion, 90 . . . microneedle sheet, 92 . . . microneedles, 1A . . . applicator, 10A . . . movable plate, 20A . . . housing, 16 . . . stopper, 17 . . . discharge port, 161 . . . stopper body, 163 . . . torsion spring (elastic member), 93 . . . liner.

The invention claimed is:

1. An applicator for applying a sheet member to skin, the applicator comprising:
   a bottom plate facing the skin;
   a top plate facing the bottom plate and configured to be pressed down toward the bottom plate;
   a bending portion configured to apply the sheet member to the skin by bending the sheet member having advanced to the bending portion in a pressed state in which the top plate has been moved toward the bottom plate; and
   a resisting portion configured to apply resistance to the sheet member advancing toward the bending portion at least in the pressed state,
wherein
   the resisting portion includes a pressing member; and an elastic member configured to provide an elastic force for pressing the pressing member against the bottom plate, and
   the resisting portion applies the resistance to the sheet member by nipping the sheet member advancing toward the bending portion with the bottom plate and the pressing member.

2. The applicator according to claim 1, further comprising a guide configured to guide the sheet member toward the bending portion in the pressed state, and to prevent advancement of the sheet member toward the bending portion in a non-pressed state in which the top plate has not been moved toward the bottom plate.

3. The applicator according to claim 1, further comprising a stopper configured to guide the sheet member toward the bending portion in the pressed state, and to prevent advancement of the sheet member toward the bending portion in a non-pressed state in which the top plate has not been moved toward the bottom plate.

4. The applicator according to claim 3, wherein
   the stopper includes a stopper body, and an elastic member providing the elastic force for pressing the stopper body against the bottom plate,
   the top plate includes a protrusion enabled to be brought into contact with the stopper body,
   in the non-pressed state, advancement of the sheet member is prevented by keeping the protrusion away from the stopper body such that the elastic force presses the stopper body against the bottom plate, and
   the protrusion is brought into contact with the stopper body and the stopper is moved away from the bottom plate in a manner resisting against the elastic force in the pressed state, such that the sheet member is guided toward the bending portion.

5. The applicator according to claim 1, further comprising an elastic member configured to generate the elastic force acting in a direction moving the bottom plate and the top plate away from each other.

6. The applicator according to claim 1, wherein the sheet member is a microneedle sheet having a plurality of microneedles provided in a manner laid along a principle surface of the sheet.

* * * * *